United States Patent
Daigo et al.

(10) Patent No.: US 9,707,321 B2
(45) Date of Patent: *Jul. 18, 2017

(54) POROUS IMPLANT MATERIAL

(75) Inventors: Yuzo Daigo, Kitamoto (JP); Shinichi Ohmori, Kitamoto (JP); Komei Kato, Saitama (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/884,203

(22) PCT Filed: Nov. 10, 2011

(86) PCT No.: PCT/JP2011/075951
§ 371 (c)(1),
(2), (4) Date: May 8, 2013

(87) PCT Pub. No.: WO2012/063907
PCT Pub. Date: May 18, 2012

(65) Prior Publication Data
US 2013/0230734 A1 Sep. 5, 2013

(30) Foreign Application Priority Data
Nov. 10, 2010 (JP) ................. 2010-251433

(51) Int. Cl.
*A61L 27/56* (2006.01)
*A61L 27/04* (2006.01)
(Continued)

(52) U.S. Cl.
CPC .............. *A61L 27/56* (2013.01); *A61L 27/04* (2013.01); *A61L 27/06* (2013.01); *B22F 3/1109* (2013.01);
(Continued)

(58) Field of Classification Search
CPC ................ A61F 2/28; A61F 2002/3092; A61F 2002/30011; A61F 2210/0076;
(Continued)

(56) References Cited

U.S. PATENT DOCUMENTS

| 4,957,819 A | 9/1990 | Kawahara et al. |
| 2007/0065712 A1 * | 3/2007 | Wada et al. ..................... 429/44 |

(Continued)

FOREIGN PATENT DOCUMENTS

| CN | 101336115 A | 12/2008 |
| EP | 1852135 A1 | 11/2007 |

(Continued)

OTHER PUBLICATIONS

International Search Report dated Jan. 24, 2012, issued for PCT/JP2011/075951.

(Continued)

*Primary Examiner* — Mark Ruthkosky
*Assistant Examiner* — Julia L Rummel
(74) *Attorney, Agent, or Firm* — Locke Lord LLP

(57) ABSTRACT

Porous implant material having a plurality of metal bodies having different porosity rates which are bonded with each other at bonded-boundary surface F parallel to a first direction, wherein: a bonded body of the metal bodies has an entire porosity rate of 50% to 92%; the metal body having higher porosity rate is a porous metal body having a three-dimensional network formed from a continuous skeleton in which a plurality of pores are interconnected; the metal body having lower porosity rate has a porosity rate of 0 to 50% and an area-occupation rate of 0.5% to 50% in a cross-section surface orthogonal to an axial direction which agrees with the first direction along the bonded-boundary surface; and a compressive strength compressing in a direction parallel to the bonded-boundary surface is 1.4 times to 10

(Continued)

times of a compressive strength compressing in a direction orthogonal to the bonded-boundary surface.

9 Claims, 6 Drawing Sheets

(51) Int. Cl.
| | | |
|---|---|---|
| *A61L 27/06* | (2006.01) | |
| *B22F 7/06* | (2006.01) | |
| *C22C 1/08* | (2006.01) | |
| *B22F 3/11* | (2006.01) | |
| *A61C 8/00* | (2006.01) | |
| *A61F 2/30* | (2006.01) | |
| *B22F 7/00* | (2006.01) | |

(52) U.S. Cl.
CPC .............. *B22F 3/1125* (2013.01); *B22F 7/06* (2013.01); *C22C 1/08* (2013.01); *A61C 8/0012* (2013.01); *A61F 2002/30011* (2013.01); *A61F 2002/30968* (2013.01); *A61F 2002/30971* (2013.01); *A61F 2310/00017* (2013.01); *A61F 2310/00023* (2013.01); *A61F 2310/00029* (2013.01); *A61F 2310/00095* (2013.01); *A61F 2310/00131* (2013.01); *A61L 2430/38* (2013.01); *B22F 7/006* (2013.01); *Y10T 428/12021* (2015.01)

(58) Field of Classification Search
CPC ............ A61F 2250/0023; B22F 1/0059; B22F 3/1109; B22F 7/002; B22F 7/004; B22F 7/006; Y10T 428/12042; Y10T 428/1253; Y10T 428/12021; Y10T 428/12479; Y10T 428/1209; Y10T 428/249953; Y10T 428/249955; Y10T 428/249956; Y10T 428/24997; Y10T 428/249978; Y10T 428/24999
See application file for complete search history.

(56) References Cited

U.S. PATENT DOCUMENTS

| | | |
|---|---|---|
| 2007/0116734 A1 | 5/2007 | Akash |
| 2009/0162235 A1 | 6/2009 | Kita et al. |
| 2010/0009103 A1 | 1/2010 | Kuboki et al. |
| 2010/0075419 A1 | 3/2010 | Inagaki et al. |
| 2011/0015743 A1* | 1/2011 | Deslauriers et al. ...... 623/17.16 |

FOREIGN PATENT DOCUMENTS

| | | |
|---|---|---|
| JP | 02-045060 A | 2/1990 |
| JP | 04-141163 A | 5/1992 |
| JP | 4164315 B2 | 3/2004 |
| JP | 4061581 B2 | 5/2004 |
| JP | 2006-263445 A | 10/2006 |
| JP | 2007-151805 A | 6/2007 |
| JP | 2008-104866 A | 5/2008 |
| JP | 2009-504207 A | 2/2009 |
| JP | 2009-516544 A | 4/2009 |
| WO | WO-2007/016796 A1 | 2/2007 |
| WO | WO-2007/108411 A1 | 9/2007 |
| WO | WO-2010/019807 A1 | 2/2010 |

OTHER PUBLICATIONS

Office Action issued in corresponding Chinese Patent Application No. CN 201180053751.4, dated Dec. 23, 2014.

* cited by examiner

POROUS IMPLANT MATERIAL

CROSS REFERENCE TO RELATED APPLICATIONS

This application is related to co-pending application, entitled, "POROUS IMPLANT MATERIAL" filed concurrently herewith in the names of Yuzo DAIGO, Shinichi OHMORI and Komei KATO as a national stage application of International Application Nos. PCT/JP2011/075948, PCT/JP2011/075949 and PCT/JP2011/075950 filed Nov. 10, 2011, which application is assigned to the assignee of the instant application and which co-pending application is also incorporated by reference herein.

BACKGROUND OF THE INVENTION

Field of the Invention

The present invention relates to material used for an implant implanted intravitally, and in particular, relates to implant material made of porous metal.

Priority is claimed on Japanese Patent Application No. 2010-251433, filed Nov. 10, 2010, the content of which is incorporated herein by reference.

Description of the Related Art

Patent Documents 1 to 3 describes implants which are implanted intravitally.

An implant (an intervertebral spacer) described in Patent Document 1 is used by inserted and arranged between centrums from which an intervertebral disk is removed. In order to easily insert the implant and prevent the implant from falling out, the implant includes a spacer body with an upper surface and a lower surface having unique figures.

An implant (a dental implant) described in Patent Document 2 is formed from: a heart material which is formed from solid-columnar titanium or titanium alloy; and a porous layer which is arranged by the heart material. The porous layer is made by sintering a plurality of spherical grains made of titanium or titanium alloy so that a plurality of continuous holes are made between the spherical grains which are bound with each other by sintering. The spherical grains each have a surface layer of gold-titanium alloy, so that the adjacent spherical grains are bound with each other by the surface layers. Accordingly, the implant described in Patent Document 2 is suggested as a small dental implant having high bound strength with a jawbone.

An implant described in Patent Document 3 is made of porous material, and includes a first part with high porosity rate and a second part with low porosity rate. In this case, for example, by inserting the second part of the implant made from absolute high-density material having a titanium-inlay-shape into a hole made at the second part of the implant having a shape of titanium foam in green and sintering them, the second part is adhered by contracting the first part. The second part with low porosity rate is used for implanting or adhesion, so that it can be prevented to waste the grains in implanting or adhesion because of the low porosity rate.

PRIOR ART DOCUMENTS

Patent Documents

Patent Document 1: Japanese Examined Patent Application, Second Publication No. 4164315
Patent Document 2: Japanese Examined Patent Application, Second Publication No. 4061581
Patent Document 3: Japanese Translation of the PCT International Publication, Publication No. 2009-504207

SUMMARY OF THE INVENTION

Problems to be Solved by the Invention

Since these implants are used for a part of intravital bone, excellent coherence to bone and appropriate strength for assuming a part of bone. However, the strength tends to fail if following the cohesion to bone; on the other hand, the cohesion to bone tends to be poor if following the strength, so that it is difficult to satisfy both of the strength and the cohesion.

The implants described in Patent Documents 2 and 3 are considered to be possible to satisfy the cohesion to bone and the necessary strength since they have a composite construction of the solid-heart material and the porous layer or a composite construction of the first part with high-porosity rate and the second part with low-porosity rate. However, if metal material is used as an implant, since metal material generally has higher strength than that of human bone, the implant may receive most of load on bone, so that stress shielding (i.e., a phenomena in which the vicinity of inserted part of the implant to bone becomes brittle) may arise.

Therefore, it is required for the implants to have the strength equivalent to that of the human bone. However, the human bone has a combined structure of bio-apatite having a dimetric crystal construction with collagen fiber, and has a strength property preferentially oriented along a C-axis direction. Accordingly, it is difficult for the implant to approach the human bone simply by combining the structures as described in Patent Documents.

The present invention is achieved in consideration of the above circumstances, and has an object to provide porous implant material having a strength property approximate to human bone, without arising stress shielding, and which is possible to maintain sufficient bound strength with human bone.

Means for Solving the Problem

Porous implant material having a plurality of metal bodies having different porosity rates which are bonded with each other at bonded-boundary surface parallel to a first direction, wherein: a bonded body of the metal bodies has an entire porosity rate of 50% to 92%; the metal body having higher porosity rate is a porous metal body having a three-dimensional network formed from a continuous skeleton in which a plurality of pores are interconnected; the metal body having lower porosity rate has a porosity rate of 0 to 50% and an area-occupation rate of 0.5% to 50% in a cross-section surface orthogonal to an axial direction which agrees with the first direction along the bonded-boundary surface; and a compressive strength compressing in a direction parallel to the bonded-boundary surface is 1.4 times to 10 times of a compressive strength compressing in a direction orthogonal to the bonded-boundary surface.

The porous implant material can be unitarily bonded to bone by easily infiltrating the bone, particularly, into the porous metal body with high porosity rate. Furthermore, since the metal body with low porosity rate is bonded, the compressive strength is large in the direction of the bonded-boundary surface. Therefore, in the bonded body, the compressive strength along the bonded-boundary surface is different from the compressive strength orthogonal to the bonded-boundary surface, so that a strength property is anisotropic as human bone. Accordingly, by implanting the porous implant material into a human body with according the anisotropic strength to a directional strength property of human bone, the stress shielding can be efficiently prevented from arising.

In this case, if the entire porosity rate is lower than 50%, the filtration of bone is slow, so that a bound function is insufficient. If the entire porosity rate is higher than 92%, the compressive strength is low, so that function as an implant of supporting bone is insufficient.

If the area-occupation rate is lower than 0.5% in the metal body with low porosity rate, the strength of the porous implant material tends to be insufficient; if higher than 50%, the infiltration of bone is slow, so that it tends to take long for the implant to be ossified.

By bonding the plurality of metal bodies, various block-like materials can be easily made.

Furthermore, in a case in which the porous implant material formed as described above is utilized as an implant, it is possible to add a porous metal body or a metal body which is bonded at a bonded-boundary surface with a different direction from the direction parallel to the first direction if required. As the metal body with low porosity, solid-metal material in which holes, voids or the like are formed such as a perforated metal, expand metal or the like can be utilized. The porosity rate is defined by a rate of volume of holes, voids or the like to an entire volume of the metal body including the holes or the voids. If the porosity rate is 0%, it is a plate-shape solid-metal material, such as a solid-plate of titanium is utilized.

In the porous implant material according to the present invention, it is preferable that: the pores formed in at least the porous metal body having the higher porosity rate be formed to have flat shaped which are long along the direction parallel to the bonded-boundary-bonded surface and short along the direction orthogonal to the bonded-boundary surface; and a length along the bonded-boundary surface be 1.2 times to 5 times of a length to orthogonal to the bonded-boundary surface in the pores.

Adding to the structure of the porous metal bodies and the metal bodies having lower porosity rate, since the pores are made flat, the directivity of the strength can be easily conferred. If a ratio of the length along the bonded-boundary surface and the length orthogonal to the bonded-boundary surface is lower than 1.2, the strength may be insufficient; if the ratio is more than 5, the pores are too low so that infiltration of bone may be too slow and the bonding may be insufficient.

In the porous implant material according to the present invention, it is preferable that the porous metal body having the higher porosity rate be foam metal made by expanding and sintering after forming expandable slurry containing metal powder and expanding agent.

The foam metal can be made so as to have the three-dimensional network structure of the continuous skeleton and the pores, and can be controlled in the porosity rate at a wide range by foam of the expanding agent. Therefore, the foam metal can be appropriately utilized according as an intended part.

Moreover, in the foam metal, an opening rate at a surface can be controlled independently of the entire porosity rate. Therefore, by raising a metallic density at the surface (i.e., reducing the opening rate), strength along the bonded-boundary surface is improved, so that anisotropic property can be easily added in combination with the strength property by a bonding structure and the flat shape of the pores.

Effects of the Invention

According to the porous implant material of the present invention, the infiltration of the bone is easier into the porous metal body. Moreover, since the metal bodies are bonded, the compressive strength along the bonded-boundary surface can be improved than the compressive strength orthogonal to the bonded-boundary surface. Furthermore, since the metal body with lower porosity rate is bonded at a prescribed area-occupation rate, the porous implant material has the strength property with anisotropic near to human bone. Therefore, by utilizing the porous implant material with according the anisotropic strength to the direction of bone, the stress shielding can be efficiently prevented from arising. Furthermore, it is easy for bone to infiltrate by the interconnected pores, so that the cohesion to bone can be is sufficiently maintained.

DETAILED DESCRIPTION OF THE INVENTION

Figure 1:
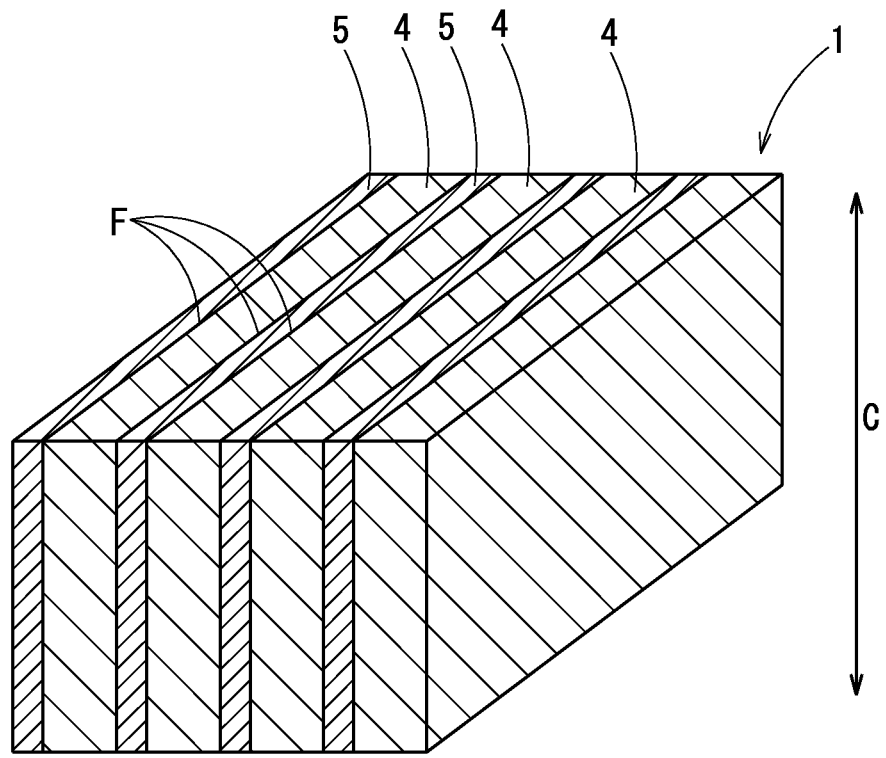
FIG. 1 is a perspective view schematically showing an embodiment of porous implant material according to the present invention.

Below, embodiments of porous implant material according to the present invention will be explained with reference to drawings.

Porous implant material 1 of the present embodiment is made by laminating, plate-like porous metal bodies 4 of foam metal having three-dimensional network structure formed from a continuous skeleton 2 in which a plurality of pores 3 are interconnected, and metal bodies 5 which are made of solid-metal material such as a perforated metal, expanded metal or the like, ordinary sintered metal material, or foam metal having low porosity rate, at bonded-boundary surfaces F parallel to a first direction. In the illustrated example, the porous metal bodies 4 and the metal bodies 5 are laminated alternately. The foam metal constructing the porous metal bodies 4 or the like is made by expanding and sintering after forming expandable slurry containing metal powder and expanding agent and the like into a sheet-shape as described later. In the foam metal, the pores 3 are open at a front surface, a back surface, and a side surface. The foam metal is made close at the vicinity of the front surface and the back surface with respect to a center part of a thickness direction.

The porous implant material 1 made by laminating the porous metal bodies 4 of the foam metal and the metal bodies 5 has an entire porosity rate of 50% to 92%. As schematically shown in FIG. 2: pores 3 in the porous metal bodies 4 with higher porosity rate are formed so as to be long along the front surface (i.e., a direction along the bonded-boundary surface F, that is a vertical direction in FIG. 2) and short along a direction orthogonal to the front surface (i.e., the thickness direction, that is a horizontal direction in FIG. 2).

In this case, each pore 3 is formed so that a length Y along the front surface (i.e., the bonded-boundary surface F) is 1.2 times to 5 times of a length X orthogonal to the front surface (i.e., the bonded-boundary surface F). In the metal bodies 5 made from solid material or ordinary sintered metal, a plurality of holes 6 are formed by a machining process or the like. Furthermore, in foam metal with lower porosity rate, since a plurality of holes, which are denoted as holes 6 in order to be distinguished from the pores 3 of the porous metal bodies 4, are formed, the pores 6 in the porous metal bodies 4 are interconnected via the holes 6. The holes 6 in the metal bodies 5 have an occupation rate of 0 to 50% to an entire volume of the metal bodies 5. In the present invention, the occupation rate of the hole 6 is also denoted as the porosity rate. If the occupation rate of the holes 6 is 0%, it is a solid-metal material having no hole 6.

In the porous implant material 1, the first direction along the bonded-boundary surface F is set to an axial direction C when implanting into a living body. The metal bodies 5 is made so that an area-occupation rate in a cross-sectional surface orthogonal to the axial direction C is set in a range of 0.5% to 50% in the entire metal bodies 5. For example, in FIG. 1, the axial direction C is set vertical; and an area-occupation rate in a horizontal cross-sectional surface orthogonal to the axial direction C (i.e., the occupation rate at an upper surface in FIG. 1) is set to 0.5% to 50%.

Figure 2:
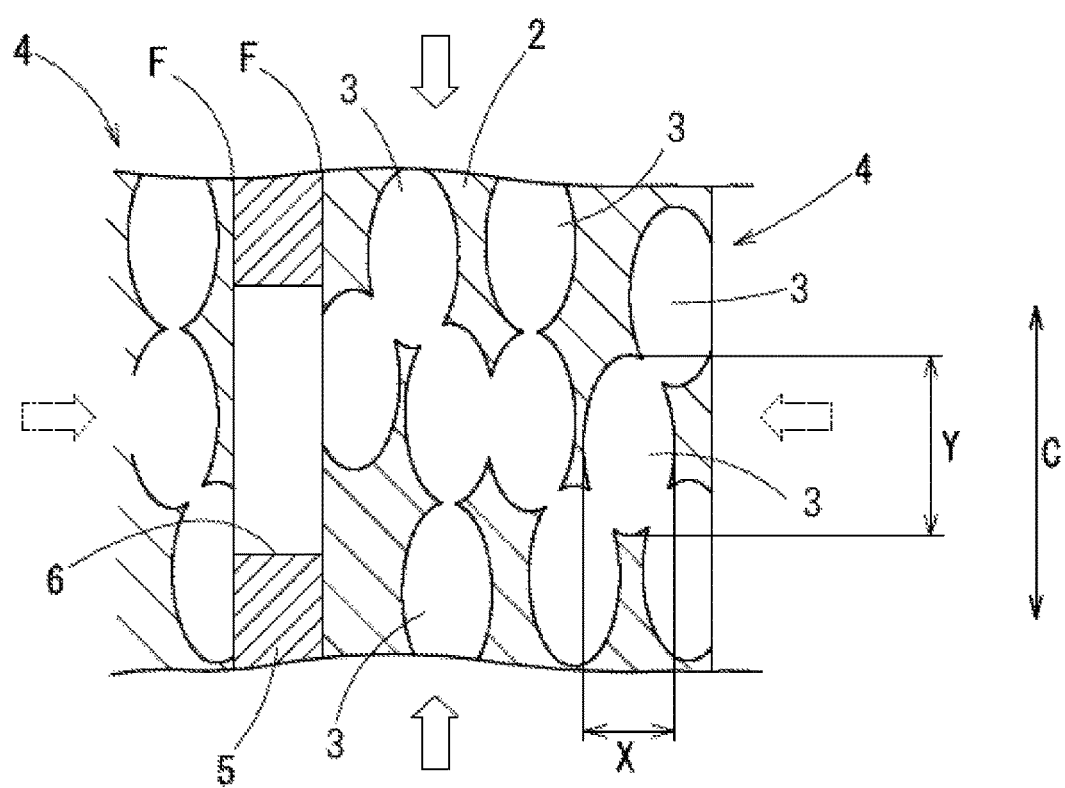
FIG. 2 is a schematic view showing a cross-section of porous metal bodies in the porous implant material shown in FIG. 1.

As a bonded body of the porous metal bodies 4 and the metal bodies 5, strength when compressing in a direction parallel to the axial direction C (i.e., a longitudinal direction of the pores 3) shown by the arrow by a continuous line in FIG. 2 is 1.4 times to 10 times of a strength when compressing in a direction parallel to a direction orthogonal to the axial direction shown by the arrow by a dotted line.

Next, a producing method of the porous implant material 1 will be explained.

The porous metal bodies 4, 5 forming the porous implant material 1 are produced by forming expandable slurry containing metal powder, expanding agent and the like into a sheet-shape by Doctor Blade method or the like, dehydrating the sheet so as to make a green sheet, and expanding the green sheet after a degreasing process and a sintering process. Furthermore, a plurality of green sheets with different mix amounts of the expanding agent from each other are made. These green sheets are layered and sintered so as to make a layered body of the porous metal bodies 4, 5. Then, by pressing or rolling the layered body to compress in a layered direction, the porous implant material 1 is produced.

The expandable slurry is obtained by kneading metal powder, binder, plasticizer, surfactant, and expanding agent with water as solvent.

As metal powder, for example, powder of metal or oxide thereof which is biologically innocuous for is used, such as pure titanium, titanium alloy, stainless steel, cobalt chromium alloy, tantalum, niobium, or the like. These powders can be produced by hydrogenate-dehydrogenate method, atomize method, chemical process method or the like. An average particle size of these powders is preferably 0.5 μm to 50 μm. These powders are contained in the slurry at 30% by mass to 80% by mass.

As the binder (i.e., a water-soluble resin binder), methyl cellulose, hydroxypropyl methylcellulose, hydroxyethyl methylcellulose, carboxymethylcellulose ammonium, ethyl cellulose, polyvinyl alcohol or the like can be used.

The plasticizer is added in order to plasticize a compact obtain by forming the slurry. As the plasticizer, for example, polyalcohols such as ethylene glycol, polyethylene glycol, glycerin and the like, oils and fats such as sardine oil, rapeseed oil, olive oil and the like, ethers such as petroleum ether and the like, and esters such as diethyl phthalate, di-n-butyl phthalate, diethylhexyl phthalate, dioctyl phthalate, sorbitan monooleate, sorbitan trioleate, sorbitan palmitate, sorbitan stearate and the like can be used.

As the surfactant, anion surfactants such as alkyl benzene sulfonate, α-olefin sulfonate, alkyl ester sulfate, alkyl ether sulfate, alkane sulfonate and the like, nonionic surface-active agent such as polyethylene glycol derivatives, polyhydric alcohol derivatives and the like, and ampholytic active agent and the like can be used.

As the expanding agent, agent which can form pores in the slurry by generating gas can be used. For example, volatile organic solvents such as pentane, neopentane, hexiane, isohexane, isoheptane, benzene, octane, toluene and the like, that is, anti-soluble hydrocarbon-system organic solvent having carbon number of 5 to 8 can be used. It is preferably that the expanding agent be contained in the expandable slurry by 0.1 to 5% by weight.

Figure 3:
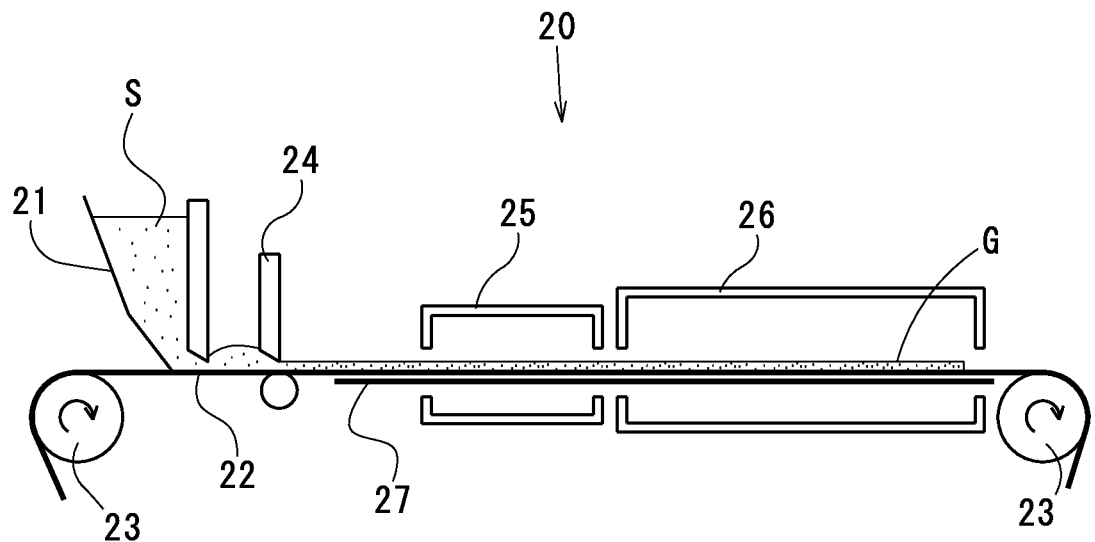
FIG. 3 is a schematic structural view showing a forming apparatus for producing the porous metal bodies.

The green sheet is formed for the porous metal bodies 4, 5 using the forming apparatus 20 shown in FIG. 3 from the expandable slurry S prepared as described above.

The forming apparatus 20 forms a sheet by Doctor Blade Method, is provided with: a hopper 21 in which the expandable slurry S is stored; a carrier sheet 22 transferring the expandable slurry S supplied from the hopper 21; rollers 23 supporting the carrier sheet 22; a blade (a doctor blade) 24 forming the expandable slurry S on the carrier sheet 22 at a prescribed thickness; a constant-temperature high-humidity chamber 25 in which the expandable slurry S is expanded; and a dehydrate chamber 26 in which the expanded slurry is dehydrated. A lower surface of the carrier sheet 22 is supported by a supporting plate 27.

Forming Process of Green Sheet

In the forming apparatus 20, at first, the expandable slurry S is charged in the hopper 21 so as to supply the expandable slurry S on the carrier sheet 22 from the hopper 21. The carrier sheet 22 is supported by the rollers 23 rotating to the right in the illustration and the supporting plate 27 so that an upper surface thereof is moved rightward in the illustration. The expandable slurry S supplied on the carrier sheet 22 is moved along with the carrier sheet 22, and formed into plate-shape by the blade 24.

Next, the plate-shape expandable slurry S is expanded in the constant-temperature high-humidity chamber 25 with a prescribed condition (ex., is 30° C. to 40° C. of temperature, 75% to 95% of humidity) with being moved for, for example, 10 minutes to 20 minutes. Subsequently, the expanded slurry S expanded in the constant-temperature high-humidity chamber 25 is dehydrated in the dehydrate chamber 26 with a prescribed condition (ex., 50° C. to 70°

C. of temperature) with being moved for, for example, 10 minutes to 20 minutes. As a result, a spongiform green sheet G is obtained.

Layering and Sintering Process

The green sheets G obtained as above and the metal bodies made by another processes are degreased and sintered in a state of being layered alternately so that the layered body of the porous metal bodies 4 and the metal bodies 5 is formed. Specifically, the binder in the green sheets G are removed (dehydrated) under a condition in vacuum, 550° C. to 650° C. of temperature for 25 minutes to 35 minutes, and then further sintered under a condition in vacuum, 700° C. to 1300° C. for 60 minutes to 120 minutes. Similar to the porous metal bodies 4, the metal bodies 5 with low porosity rate are made from pure titanium, titanium alloy, stainless steel, cobalt chromium alloy, tantalum, niobium, and the like.

In the layered body of the porous metal bodies 4 and the metal bodies 5 as obtained above, the porous metal bodies 4 have three-dimensional network structures formed from continuous skeletons in which a plurality of pores 3 are interconnected. The porous metal bodies 4 are produced by foaming and sintering the green sheet molded on the carrier sheet 22 so that densities at vicinities of a surface being in contact with the carrier sheet 22 and the counter surface thereof, that is, the densities at the vicinities of a front surface and a back surface, are closer than that of a center part along a thickness direction to have high metallic density. In the porous metal bodies 4, the pores 3 are open at the front surface and the back surface. Therefore, also in the layered body of the porous metal bodies 4, the pores 3 are interconnected from the front surface to the back surface.

If making the from foam metal with lower porosity rate, metal bodies 5 also have a three-dimensional network structure. If making from solid-metal material, the metal bodies 5 are diffusion-bonded to the porous metal bodies 4 by heat of sintering the porous metal bodies 4.

Compression Process

Next, the layered body of the porous metal bodies 4 and the metal bodies 5 is is compressed in the thickness direction (i.e., layered direction) by pressing or rolling at a prescribed pressure.

By the compression process, the porous metal body 4 with higher porosity rate is compressed antecedently. Accordingly, the inner pores 3 are pressed so as to have oblong shapes long along the front surface (i.e., along the bonded-boundary surface) and short orthogonal to the front surface (i.e., along the thickness direction). If the pores 3 are oblong, as the porous metal body 5, a compressive strength is higher when compressed in a longitudinal direction of the oblong shape than a compressive strength when compressed orthogonal to the longitudinal direction of the oblong shape. In addition, in a case in which the metal bodies 5 are made from solid-metal material or ordinary sintered metal, the metal bodies 5 are not pressed in the compression process. Also in a case in which the metal bodies 5 are made from foam metal, since the porosity rate is low, the metal bodies 5 are hardly pressed in the compression process, so that the pores are maintained substantially spherically; however, it may be slightly pressed.

Furthermore, the porous metal bodies 4, 5 have the high density in the vicinities of the front surface and the back surface thereof. Therefore, the layered body thereof has the higher density in the vicinities of the bonded-boundary surfaces F than at the center part between the bonded-boundary surfaces F.

In the layered body, the metal bodies 5 made of solid-metal material, foam metal with lower porosity rate, or ordinary sintered metal are bonded, the pores 3 in the porous metal bodies 4 with higher porosity rate are pressed so as to have oblong shaped long along the bonded-boundary surfaces F, and the density of the porous metal bodies 4 is high in the vicinities of the bonded-boundary surfaces F. Therefore, the strength when being compressed in the bonded-boundary surfaces F (i.e., in the direction shown by the arrow by the continuous line in FIG. 2) is higher than the strength when being compressed orthogonal to the bonded-boundary surfaces F (i.e., in the thickness direction shown by the arrow by the dotted line in FIG. 2).

Next, the layered body of the porous metal material bodies 4 and the metal bodies 5 is cut into a desired shape. An axial direction C is set as a first direction along the bonded-boundary surfaces F. The layered body is cut so that, in a cross section orthogonal to the axial direction C, an occupation area by the metal bodies 5 is 0.5% to 50% of a total area.

In the porous implant material 1 as produced above, owing to the porosity having the porosity rate of 50% to 92% in total, it is easy to infiltrate for bone when the porous implant material 1 is used as an implant, so that the cohesion to the bone is excellent. Moreover, since the compressive strength is anisotropic; and the porous implant material 1 has the strength property near to the human bone. Therefore, when the porous implant material 1 is used as a part of the bone, by implanting into a human body with according the anisotropic strength to a directional strength property of the human bone, the stress shielding can be efficiently prevented from arising. Specifically, it is preferable that the axial direction C along the bonded-boundary surfaces F of the porous implant material 1 agree with a C-axis direction of the bone.

Figure 4:
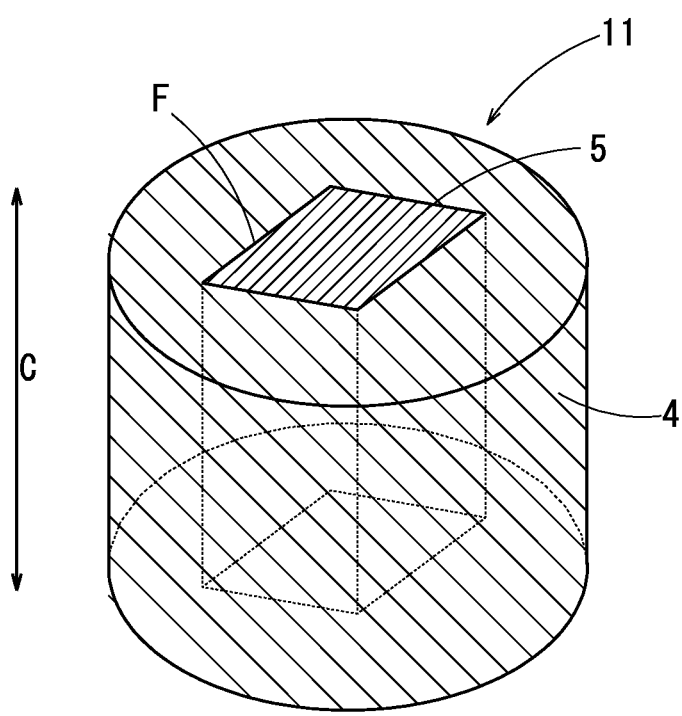
FIG. 4 is a plan view schematically showing another embodiment of the porous implant material.

The human bone is structured from a sponge bone at the center part thereof and a cortical bone surrounding the sponge bone. When the porous implant material is used as the sponge bone, the compressive strength in the axial direction C is preferably 4 to 70 MPa; and an elastic module of the compression is preferably 1 to 5 GPa. When the porous implant is used as the cortical bone, the compressive strength in the axial direction C is preferably 100 to 200 MPa, and the elastic module of the compression is preferably 5 to 20 GPa. In each case, it is preferable that the compressive strength in the axial direction C be directional so as to be 1.4 times to 10 times of the compressive strength of the compressive strength in the direction orthogonal to the axial direction C FIG. 4 shows another embodiment. In the abovementioned embodiment, the porous metal bodies 4 and the metal bodies 5 are formed into plate-shapes and layered. In a porous implant material 11 this embodiment, the metal body 5 formed into a columnar-shape is surrounded by the porous metal body 4 with higher porosity rate, so that the porous implant material is formed into a columnar-shape. Therefore, the bonded-boundary surface F is formed as a cylindrical surface. The axial direction C agrees with a longitudinal direction of the columnar-shape.

The porous implant material 11 is produced by: forming the green sheet by Doctor Blade Method as described above; combining the green sheet with the metal body 5 by winding the green sheet around the metal body 5; sintering in the combination so as to make a columnar-shaped sintered body (in which the metal body 5 is the center part and the porous metal body 4 surrounds the metal body 5); and compressing the sintered body in a radial direction thereof by rolling. By compressing the sintered body by rolling, the pores in the porous metal body 4 with higher porosity rate are pressed radially so as to have oblong-shapes which are bent along the longitudinal direction and a circumferential direction of the columnar-shape.

Therefore, the porous implant material 11 has the higher compressive strength in the longitudinal direction of the columnar-shape (i.e., along the axial direction C) as compared with the compressive strength in the radial direction. Therefore, the porous implant material 11 is implanted so that the axial direction C agrees with the strength property of the bone.

Examples

The green sheets were made by the expanding slurry method, and then the porous metal bodies were made from the green sheets. As material, metal powder of titanium having an average particle size of 20 μm, polyvinyl alcohol as a binder, glycerin as a binder, alkyl benzene sulfonate as surfactant, and heptane as expanding agent are kneaded with water as solvent, so that slurry was made. The slurry was formed into a plate-shape and dehydrated, so that the green sheets were made. In this case, by varying mixing ratio or the like of the expanding agent in the slurry, two types of the green sheets were produced so as to have different porosity rate after foaming. Subsequently, the two types of the green sheets were layered alternately, degreased and sintered, so that layered body of the porous metal bodies with high porosity rate and the metal bodies with low porosity rate was obtained. Furthermore, compressing the layered body by a rolling machine and cutting so as to have the proper area-occupation rate of the metal body with low porosity rate, so that various implant material are produced.

Figure 5:
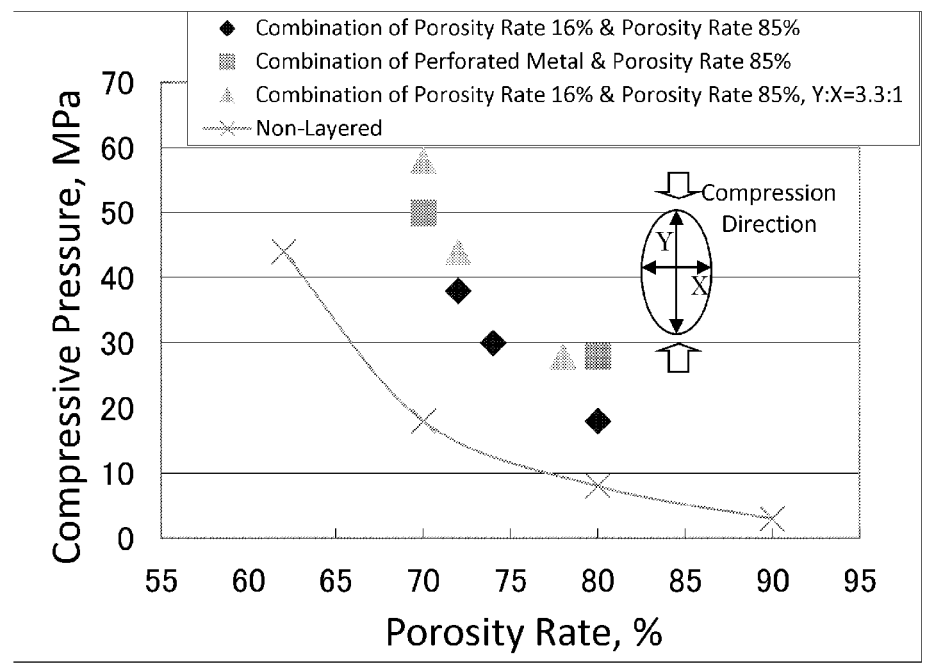
FIG. 5 is a graph showing degrees of dependence of compressive strengths on porosity rates and pore-shapes in the porous implant material of examples.

FIG. 5 is a graph showing degrees of dependence of the compressive strengths on the porosity rate and the like. In FIG. 5, "combination of porosity rate 16% and porosity rate 85%" denotes a combination of porous metal bodies having porosity rate of 85% and metal bodies having porosity rate of 16%. Entire porosity rate was controlled by varying the layering number of the metal bodies so that the area-occupation rate of the metal bodies with low porosity rate becomes 10%, 15%, or 20%.

In "combination of perforated metal and porosity rate 85%", a perforated metal made of titanium having holes of 2 mm diameter with opening rate (porosity rate) of 20% was used as the metal bodies. Also in this case, in order to control the entire porosity rate, the layering number of the metal bodies was varied so that the area-occupation rate of the metal bodies becomes 10% or 20%.

In "combination of porosity rate 16% and porosity rate 85%, Y:X=3.3:1", a combination of the porous metal body having the porosity rate of 85% and the metal body having the porosity rate of 16% was compressed, so that the pores in the porous metal body were made flat. That is, in the flat shape, a ratio the length Y along the direction parallel to a compressed surface by the rolling machine and the length X along the direction orthogonal to the compressed surface (Y/X, that is a "prolate degree") was Y:X=3.3:1. Prolate degree of the pores in each sample was obtained by: selecting five to ten pores in which the shapes thereof were easy to be certified in a photo image by an optical microscope; calculating the prolate degrees from lengths Y and X of the selected pores from the photo image; and averaging the prolate degrees.

Moreover, comparative examples denoted as "non-layered" in the drawing were made from only a porous metal body having the porosity rate of 85%.

The compressive strengths were measured according to JIS H 7920 (Method for Compressive Test of Porous Metals).

As shown in FIG. 5, the examples had higher compressive strength than "non-layered" comparative examples, so that appropriate implants having a wide range of the compressive strength can be produced by adjusting the porosity rate appropriately.

The present invention is not limited to the above-described embodiments and various modifications may be made without departing from the scope of the present invention.

For example, in the above embodiments, two types of the porous metal bodies having the different porosity rates, i.e., the porous metal bodies with higher porosity rate and the porous metal bodies with lower porosity rate, are bonded. However, three or more types of porous metal bodies each having different porosity rate may be bonded.

Figure 6:
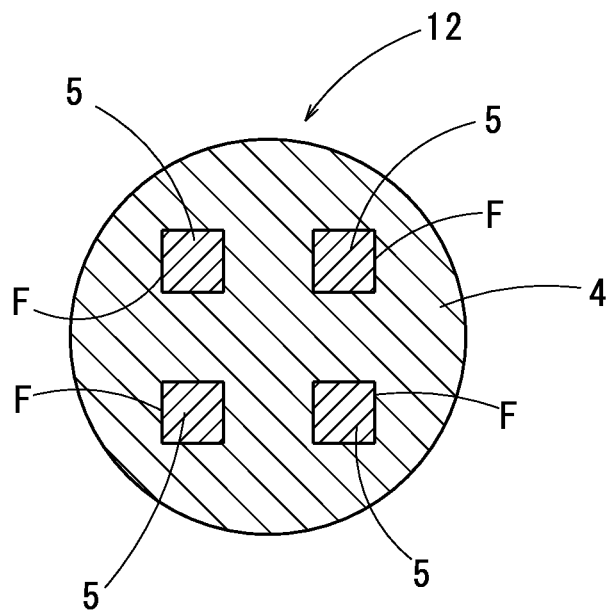
FIG. 6 is a plan view showing another embodiment of the present invention.
Figure 7:
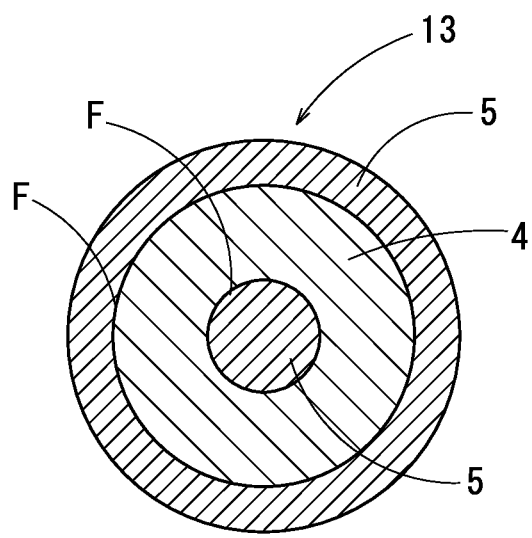
FIG. 7 is a plan view showing another embodiment of the present invention.
Figure 8:
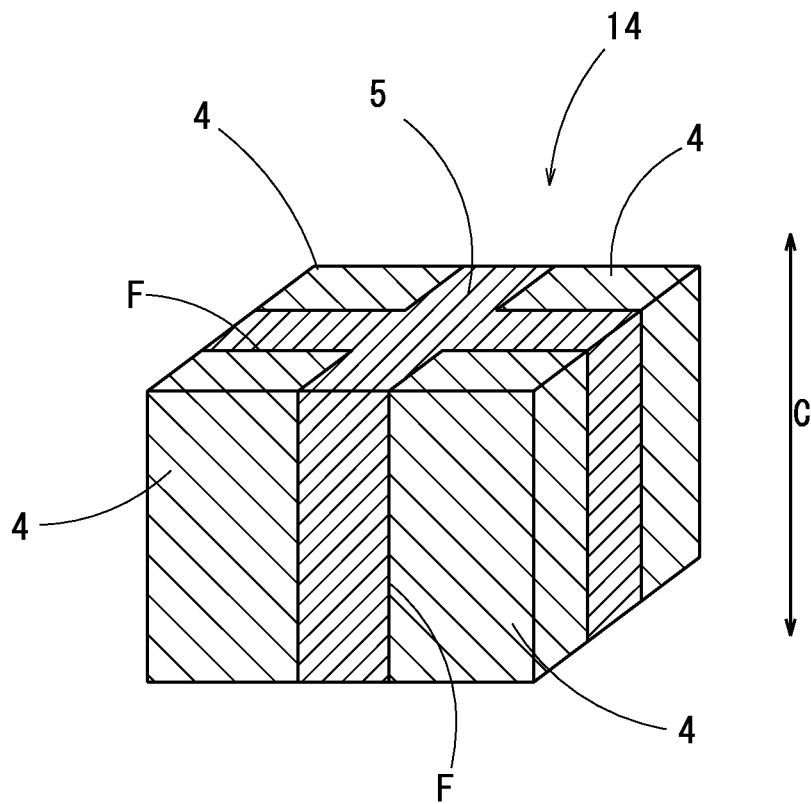
FIG. 8 is a perspective view showing another embodiment of the present invention.

When a plurality of porous metal bodies are bonded, various configurations may be carried out as shown in FIGS. 6 to 8 besides the configurations in which the plate-shape porous metal bodies are layered as the above embodiments. In these drawings, the porous metal bodies each having the different porosity rates are denoted by the same reference symbols as in FIG. 1; that is, the porous metal bodies with higher porosity rates are denoted by the reference symbol "4", and the metal bodies with lower porosity rates are denoted by the reference symbol "5". For example, in a porous implant material 12 shown in FIG. 6, the plurality of columnar-shaped metal bodies 5 with lower porosity rate than in FIG. 4 are provided; in a porous implant material 13 shown in FIG. 7, the metal bodies 5 with low porosity rate and the porous metal body 4 with high porosity rate are multiply arranged concentrically; and in a porous implant material 14 shown in FIG. 8, the metal body 5 with low porosity rate is formed into a cross-shaped block, and the porous metal bodies 4 with high porosity rate which are formed into rectangular blocks are combined at four corners of the metal body 5. In the producing processes, the porous implant materials can be made by winding a plate-shape porous metal body around a particular metal body, or by rounding a plate-shape porous metal body. Prolate direction of the pores is illustrated as C-direction in FIG. 8. The prolate directions of the pores in FIGS. 6, 7 are orthogonal to pages.

As a bonding method, a method in which the porous metal bodies are each sintered, and then assembled and diffusion-bonded, can be accepted besides the method in which the green sheets are assembled and then sintered. When compressing, the bonded bodies having the columnar configuration shown in FIG. 6 and FIG. 7 can be compressed in the radial direction by rolling the bonded bodies of the porous metal bodies as the embodiment shown in FIG. 4. Also, the compression process can be carried out in the state of the green sheets before sintering, or after sintering.

In each case, it is important that the bonded-boundary surfaces F are parallel to the first direction: Consequently, in combination with the directional strength of the compressed pores, the compressive strength along the direction parallel to the bonded-boundary surface F can be higher than the compressive strength along the direction orthogonal to the bonded-boundary surface F. Moreover, when using as an implant, another porous metal body or metal body having lower porosity rate can be added that is bonded at a bonded-boundary surface along the other direction than the direction parallel to the prolate direction of the pores (i.e., parallel to the first direction) as appropriate if the directivity of the intended strength can be maintained.

Figure 9:
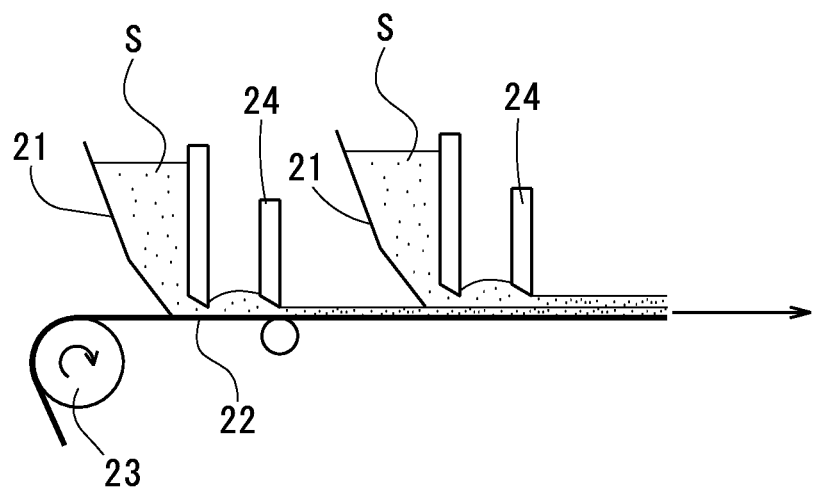
FIG. 9 is a schematic structural view showing a substantial part of another forming apparatus for producing the porous metal bodies.

When forming the slurry into a sheet-shape by Doctor Blade Method, the green sheets can be formed in a layered state by supplying expandable slurries each having different mixing rate of the expanding agent in a layered state from a plurality of hoppers as shown in FIG. 9.

Furthermore, a method of decompression-foaming can be accepted besides the method of expanding and forming by Doctor Blade Method. Specifically, pores and dissolved gas are once removed from the slurry, and then the slurry is stirred while adding gas, so that expandable slurry is made into a state in which bubble nucleus of the added gas are made and distributed therein. Subsequently, the slurry including the bubble nucleus is decompressed to a prescribed pressure and maintained at pre-cooling temperature higher than freezing point and lower than boiling point of the slurry at the prescribed pressure, so that the bubble nucleus are expanded and the slurry in which volume thereof is increased by the expansion of the bubble nucleus is vacuum-freeze dried. By sintering the green body obtained as abovementioned, porous sintered body can be produced.

INDUSTRIAL APPLICABILITY

The implant material of the present invention can be used which is implanted into a living body as an implant such as an intervertebral spacer, a dental implant and the like.

DESCRIPTION OF REFERENCE SYMBOLS 1 porous implant material
2 skeleton
4 porous metal body with high porosity rate
5 metal body with low porosity rate
11 porous implant material
12 to 14 porous implant material
F bonded-boundary surface
C axial direction

What is claimed is:
1. A porous implant material, comprising:
a first set of metal bodies; and
a second set of porous metal bodies having a higher porosity than and bonded to the metal bodies of the first set in an alternating manner, the metal bodies of the first and second sets bonded with each other at a bonded-boundary surface parallel to a first direction;
wherein the implant material has a total porosity rate of 50 to 92%,
each of the porous metal bodies of the second set has a three-dimensional network formed from a continuous skeleton in which a plurality of pores are interconnected, and in which the pores are long along the direction parallel to the bonded-boundary surface and short along the direction orthogonal to the bonded-boundary surface,
each of the metal bodies of the first set has a porosity rate of 0.5 to 50%, substantially spherical pores that are more spherical than the pores in the porous metal bodies of the second set, and a thickness less than a respective thickness of each of the porous metal bodies of the second set, and
a compressive strength compressing in a direction parallel to the bonded-boundary surface is 1.4 times to 10 times a compressive strength compressing in a direction orthogonal to the bonded-boundary surface; and
wherein the porous implant material is structurally configured for use as one of
(i) a sponge bone with a compressive strength in the direction parallel to the bonded-boundary surface of 4 to 70 MPa and a compressive elastic modulus in the direction parallel to the bonded-boundary surface of 1 to 5 GPa, and
(ii) a cortical bone with a compressive strength of 100 to 200 MPa and a compressive elastic modulus in the direction parallel to the bonded-boundary surface of 5 to 20 GPa.

2. The porous implant material according to claim 1, wherein
the pores in the second set of porous metal bodies are situated such that their lengths in the direction parallel to the bounded boundary surface is 1.2 to 5 times their lengths in the direction orthogonal to the bonded boundary surface.

3. The porous implant material according to claim 1, wherein
at least one of the porous metal bodies of the second set is foam metal made by expanding and sintering after forming an expandable slurry containing metal powder and an expanding agent.

4. The porous implant material according to claim 2, wherein
at least one of the porous metal bodies of the second set is foam metal made by expanding and sintering after forming an expandable slurry containing metal powder and an expanding agent.

5. The porous implant material according to claim 1, wherein the metal bodies of the first set define a plurality of holes therethrough.

6. The porous implant material according to claim 5, wherein the plurality of holes provide each of the metal bodies of the first set with a porosity between 0.5% and 50%.

7. The porous implant material according to claim 5, wherein the plurality of holes in a respective metal body of the first set connect pores disposed in porous bodies of the second set disposed on opposite sides of the respective metal body of the first set.

8. The porous implant material according to claim 1, wherein at least one metal body of the first set is bonded to a pair of porous metal bodies of the second set, and at least one porous metal body of the second set is bonded to a pair of metal bodies of the first set.

9. The porous implant material according to claim 1, wherein
when the first direction along the bonded-boundary surface is set to an axial direction, a proportion of the first set to a total area of a cross-sectional surface perpendicular to the bonded-boundary surface is 0.5% to 50%.

* * * * *